US012396773B1

(12) United States Patent
Wu et al.

(10) Patent No.: US 12,396,773 B1
(45) Date of Patent: Aug. 26, 2025

(54) AUTOMATIC BONE CEMENT MIXING AND INJECTION DEVICE

(71) Applicant: Suzhou Feima Medical Technology Co., Ltd., Jiangsu (CN)

(72) Inventors: Shuce Wu, Jiangsu (CN); Qinglei Cui, Jiangsu (CN)

( * ) Notice: Subject to any disclaimer, the term of this patent is extended or adjusted under 35 U.S.C. 154(b) by 0 days.

(21) Appl. No.: 19/048,793

(22) Filed: Feb. 7, 2025

(30) Foreign Application Priority Data

Feb. 23, 2024 (CN) .......................... 202410200317.3

(51) Int. Cl.
*A61B 17/88* (2006.01)
(52) U.S. Cl.
CPC .. *A61B 17/8833* (2013.01); *A61B 2017/8838* (2013.01)
(58) Field of Classification Search
CPC ................... A61B 17/8833; A61B 2017/8838
See application file for complete search history.

(56) References Cited

U.S. PATENT DOCUMENTS

| 4,277,184 | A | * | 7/1981 | Solomon | ............ | A61B 17/8825 |
| | | | | | | 366/139 |
| 5,842,786 | A | * | 12/1998 | Solomon | ................ | B01F 31/40 |
| | | | | | | 366/139 |
| 8,167,835 | B2 | * | 5/2012 | Keller | .................... | B05C 17/01 |
| | | | | | | 604/82 |
| 11,737,802 | B1 | * | 8/2023 | Williams | ........... | A61B 17/8827 |
| | | | | | | 606/94 |
| 2019/0038331 | A1 | | 2/2019 | Purdy et al. | | |

FOREIGN PATENT DOCUMENTS

| CN | 203369946 U | 1/2014 |
| CN | 105147384 A | 12/2015 |
| CN | 109069753 A | 12/2018 |
| CN | 209392078 U | 9/2019 |
| CN | 212699095 U | 3/2021 |
| CN | 212819279 U | 3/2021 |
| CN | 215463513 U | 1/2022 |
| CN | 219048898 U | 5/2023 |
| CN | 219354127 U | 7/2023 |
| CN | 219645855 U | 9/2023 |
| CN | 117426852 A | 1/2024 |
| KR | 20210037869 A | 4/2021 |

* cited by examiner

Primary Examiner — Nicholas W Woodall

(57) ABSTRACT

An automatic bone cement mixing and injection device, comprising a cylindrical structure, a sliding block, a mixer, pistons, a mixer driving device and a piston driving device; two ends of the cylindrical structure are respectively an open installation port and a narrowed injection port, a feed port is arranged on one side wall of the cylindrical structure; one end of the mixer passes through the installation port of the cylindrical structure and is placed inside the cylindrical structure, and the other end is connected to a rotating shaft of the mixer driving device; one end of each piston passes through the installation port of the cylindrical structure and is placed inside the cylindrical structure, and the other end of each piston is pressed against the sliding block; the sliding block is connected to the piston driving device and is driven by the piston driving device to make linear motion.

6 Claims, 2 Drawing Sheets

AUTOMATIC BONE CEMENT MIXING AND INJECTION DEVICE

1. TECHNICAL FIELD

The invention relates to the technical field of medical surgery, in particular to an automatic bone cement mixing and injection device.

2. BACKGROUND ART

Bone cement, as a widely used medical material in orthopedic surgery, is named for its unique physical properties and its appearance and shape after setting, which resemble those of ordinary white cement used in construction. As a common implant in the body, bone cement has a wide range of applications in the medical field, playing a key role particularly in procedures such as vertebroplasty and joint replacement surgery. With the continuous improvement of medical levels in China, the usage of bone cement has also shown a trend of year-on-year growth.

The use of bone cement primarily involves two crucial processes: mixing and injection. Prior to the surgery, the doctor needs to combine the solid and liquid ingredients and manually mix them for several minutes to ensure uniform mixing of the bone cement. Following this, the doctor transfers the well-mixed bone cement to a syringe, preparing it for injection.

However, the existing bone cement mixing devices currently developed by researchers still have some shortcomings. Firstly, most of these devices rely on manual operation, using tools with mixing blades, which is both time-consuming and laborious. Secondly, these devices typically only have mixing functionality and lack injection capabilities, meaning that doctors need to switch tools after mixing to perform the injection, adding complexity to the operation. Finally, since the injection of bone cement requires precise control of the injection volume, doctors often need to frequently move between the operating table and the medical imaging room to control the injection volume by observing the images; this approach not only prolongs the surgery time, but also brings inconvenience to the medical staff's operation, increasing the exposure of operators and/or patients to radiation.

In order to address these problems, patents CN202221323452.X and CN201120395926.7 propose two bone cement mixing devices. Patent CN202221323452.X presents a micro electric mixer, which uses a motor to drive spiral blades to rotate, transporting the raw materials from the bottom of the centrifuge tube to the upper end for mixing, thus improving mixing efficiency. However, this device still has some limitations, such as the inability to adjust the mixing speed, its unsuitability for direct injection operations, and the lack of remote operation capabilities.

On the other hand, patent CN201120395926.7 introduces a convenient mixing and injection device for bone cement. This device cleverly combines the mixing frame and the syringe body, achieving an integrated operation for both mixing and injection. The bone cement can be mixed by rotating the mixing handle, while pressing the handle downward allows for injection. This design simplifies the operation process and improves surgical efficiency. However, the device also has some drawbacks, such as both mixing and injection operations being manual, the inability to achieve automation, and the lack of remote operation capabilities.

In summary, although these two bone cement mixing devices have solved the problems existing in the traditional surgical preparation process to a certain extent, there are still some limitations that need to be further improved and perfected.

3. SUMMARY OF THE INVENTION

The object of the invention is to propose an automatic bone cement mixing and injection device, which features automatic adjustment of mixing speed and integrates both mixing and injection functions, and can meet a wider range of clinical needs, improve surgical efficiency, and enhance the convenience and effectiveness of bone cement surgeries.

In order to realize the above objects, the technical scheme of the invention is as follows: an automatic bone cement mixing and injection device, comprising a cylindrical structure, a sliding block, a mixer, pistons, a mixer driving device and a piston driving device; two ends of the cylindrical structure are respectively an open installation port and a narrowed injection port, a feed port is arranged on one side wall of the cylindrical structure; one end of the mixer passes through the installation port of the cylindrical structure and is placed inside the cylindrical structure, and the other end is connected to a rotating shaft of the mixer driving device; one end of each piston passes through the installation port of the cylindrical structure and is placed inside the cylindrical structure, and the other end of each piston is pressed against the sliding block; the sliding block is connected to the piston driving device and is driven by the piston driving device to make linear motion.

The sliding block is composed of an upper sliding block, a lower sliding block, a bearing and a retaining ring; the upper sliding block and the lower sliding block are provided with grooves that match an outer ring of the bearing; the bearing is placed in the grooves, and the retaining ring is pressed against the bearing; the other end of each piston is pressed against the retaining ring of the sliding block.

The installation port is provided with an end cover that cooperates with the mixer and the pistons and seals the installation port.

A plurality of blades are arranged at one end of the mixer installed inside the cylindrical structure; the blades are arranged along an axial direction of the mixer; an installation and movement space for each piston is formed between two adjacent blades and a cylinder wall of the cylindrical structure.

The blades are provided with through holes to facilitate the mixing of bone cement.

One end of each piston installed inside the cylindrical structure is provided with a columnar structure that fits tightly with the adjacent blades and the cylinder wall.

A nut is fixed on the sliding block; a screw rod is fixed on an output shaft of the piston driving device; the nut is installed on the screw rod. In this process, the cooperation between the nut and the sliding block ensures that each piston only performs linear motion.

The working principle of the invention is as follows:
 mixing action: when the mixer driving device is activated, it drives the mixer and the pistons mounted on it to rotate, thereby achieving uniform mixing of the bone cement;
 injection action: when the piston driving device is activated, a series of mechanical connections transfer linear motion to the three pistons, pushing the bone cement along the axial direction of the mixer for injection.

The invention integrates the mixing and injection of bone cement through a uniquely designed combination of the pistons and mixer; it features a high degree of automation, using electric drive for both the mixing and injection processes, thereby reducing the overall surgery time, lightening the physical burden on the operator, and minimizing the exposure of both the operator and/or the patient to radiation.

4. BRIEF DESCRIPTION OF ACCOMPANYING DRAWINGS

5. SPECIFIC EMBODIMENT OF THE INVENTION

Figure 1:
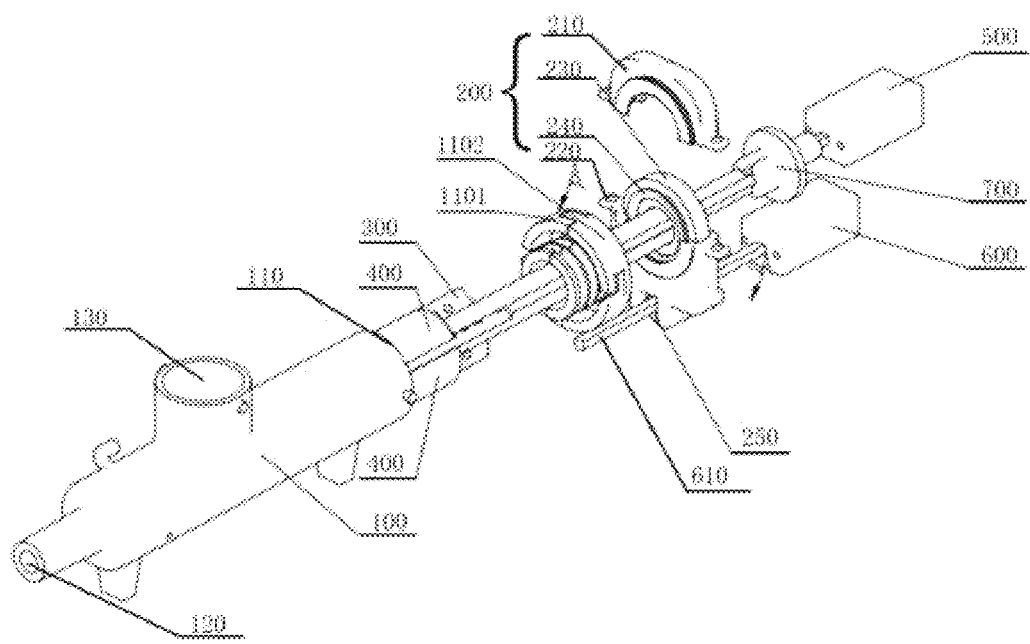
FIG. 1 is a schematic diagram of the assembly of the components of the invention.

In order to make the objects, technical schemes and advantages of the embodiments of the invention clearer, the technical schemes in the embodiments of the invention will be clearly and completely described below in combination with the accompanying drawings in the embodiments of the invention, obviously, the described embodiments are some, but not all embodiments of the invention. The components of the embodiments of the invention generally described and illustrated in the drawings herein may be arranged and designed in a variety of different configurations. Therefore, the following detailed description of the embodiments of the invention provided in the accompanying drawings is not intended to limit the scope of the claimed invention, but is merely representative of selected embodiments of the invention. Based on the embodiments in this invention, all other embodiments obtained by those of ordinary skill in the art without making creative efforts shall fall within the protection scope of this invention.

Figure 2:
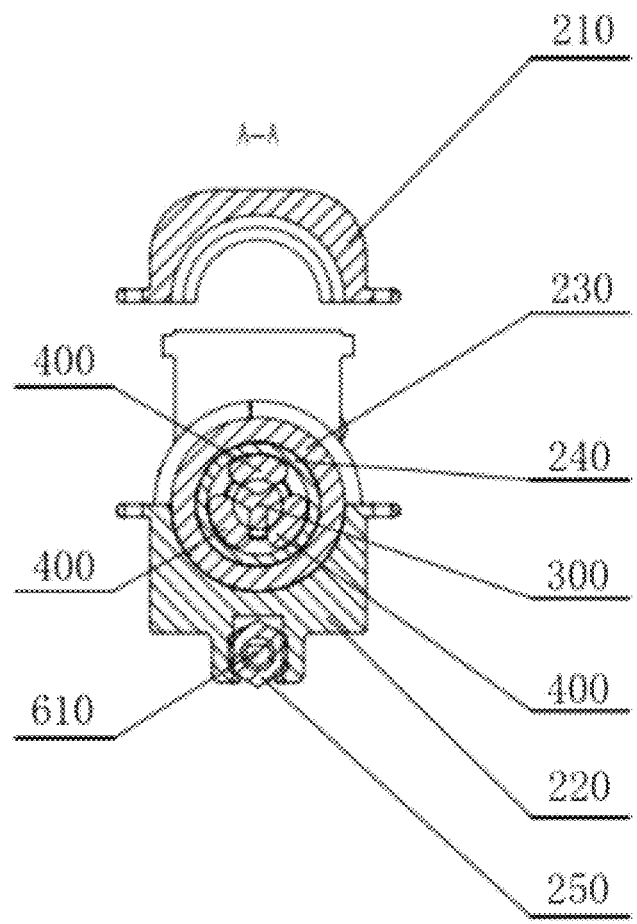
FIG. 2 is a cross-sectional view of the A-A plane in FIG. 1.
Figure 3:
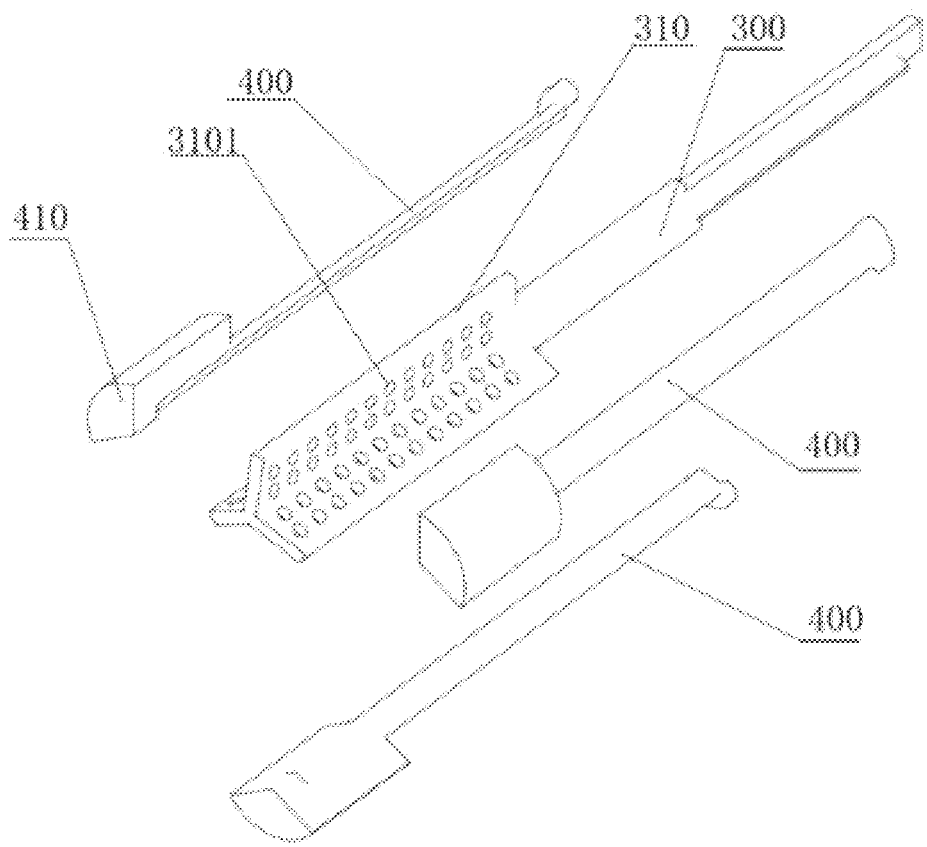
FIG. 3 is an exploded view of the pistons and mixer in the invention.

As shown in FIGS. 1 and 2, an automatic bone cement mixing and injection device of the invention comprises a cylindrical structure 100, a sliding block 200, a mixer 300, pistons 400, a mixer driving device 500 and a piston driving device 600; two ends of the cylindrical structure 100 are respectively an open installation port 110 and a narrowed injection port 120, a feed port 130 is arranged on one side wall of the cylindrical structure 100, and the feed port 130 can be completely sealed after the feeding is completed; one end of the mixer 300 passes through the installation port 110 of the cylindrical structure 100 and is placed inside the cylindrical structure 100, and the other end is connected to a rotating shaft of the mixer driving device 500, this connection can be direct or indirect, this connection method in this embodiment is to connect through a coupling 700; the sliding block 200 is connected to the piston driving device 600 and is driven by the piston driving device 600 to make linear motion; the sliding block 200 is composed of an upper sliding block 210, a lower sliding block 220, a bearing 230 and a retaining ring 240; the upper sliding block 210 and the lower sliding block 220 are provided with grooves that match an outer ring of the bearing 230; the bearing 230 is placed in the grooves, and the retaining ring 240 is pressed against the bearing 230; one end of each piston 400 passes through the installation port 110 of the cylindrical structure 100 and is placed inside the cylindrical structure 100, and the other end of each piston 400 is pressed against the retaining ring 240 of the sliding block 200.

The installation port 110 is provided with an end cover that cooperates with the mixer 300 and the pistons 400 and seals the installation port 110; the end cover in this embodiment is composed of a left end cover 1101 and a right end cover 1102.

A plurality of blades 310 are arranged at one end of the mixer 300 installed inside the cylindrical structure 100; in this embodiment, three blades 310 are provided; the blades 310 are arranged along an axial direction of the mixer 300; an installation and movement space for each piston 400 is formed between two adjacent blades 310 and a cylinder wall of the cylindrical structure 100.

The blades 310 are provided with through holes 3101 to facilitate the mixing of bone cement.

One end of each piston 400 installed inside the cylindrical structure 100 is provided with a columnar structure 410 that fits tightly with the adjacent blades 310 and the cylinder wall.

A nut 250 is fixed on the sliding block 200, and the nut 250 in this embodiment is fixed below the lower sliding block 220; a screw rod 610 is fixed on an output shaft of the piston driving device 600, and the nut 250 is installed on the screw rod 610. In this process, the cooperation between the nut 250 and the sliding block 200 ensures that each piston 400 only performs linear motion.

The mixer driving device 500 and the piston driving device 600 in this embodiment both use electric motors, but this choice does not limit the protection scope of the invention. Any device that can achieve the same technical effect and manual operation are within the protection scope claimed by the invention.

In another embodiment of the invention, a remote wireless operating device may be included. The control device arranged on the main body of the automatic bone cement mixing and injection device of the invention receives the signal of the remote wireless operating device and controls the mixer driving device and the piston driving device according to the instruction. For those skilled in the art, the remote wireless operating device and the control device are based on existing electrical and automation technologies.

The above description is only a preferred embodiment of the invention and is not intended to limit the invention. For those skilled in the art, the invention may have various modifications and variations. Any modification, equivalent substitution, improvement, etc. made within the spirit and principle of the invention shall be included in the protection scope of the invention.

The invention claimed is:

1. An automatic bone cement mixing and injection device, comprising a cylindrical structure, a sliding block, a mixer, pistons, a mixer driving device and a piston driving device; two ends of the cylindrical structure are respectively an open installation port and a narrowed injection port, a feed port is arranged on one side wall of the cylindrical structure; one end of the mixer passes through the installation port of the cylindrical structure and is placed inside the cylindrical structure, and the other end is connected to a rotating shaft of the mixer driving device; one end of each piston passes through the installation port of the cylindrical structure and is placed inside the cylindrical structure, and the other end of each piston is pressed against the sliding block; the sliding block is connected to the piston driving device and is driven by the piston driving device to make linear motion; a plurality of blades are arranged at one end of the mixer installed inside the cylindrical structure; the blades are arranged along an axial direction of the mixer; an installation and movement space for each piston is formed between two adjacent blades and a cylinder wall of the cylindrical structure.

2. The automatic bone cement mixing and injection device of claim 1, wherein the sliding block is composed of an upper sliding block, a lower sliding block, a bearing and a retaining ring; the upper sliding block and the lower sliding block are provided with grooves that match an outer ring of the bearing; the bearing is placed in the grooves, and the retaining ring is pressed against the bearing; the other end of each piston is pressed against the retaining ring of the sliding block.

3. The automatic bone cement mixing and injection device of claim 1, wherein the installation port is provided with an end cover that cooperates with the mixer and the pistons and seals the installation port.

4. The automatic bone cement mixing and injection device of claim 1, wherein the blades are provided with through holes to facilitate the mixing of bone cement.

5. The automatic bone cement mixing and injection device of claim 1, wherein one end of each piston installed inside the cylindrical structure is provided with a columnar structure that fits tightly with the adjacent blades and the cylinder wall.

6. The automatic bone cement mixing and injection device of claim 1, wherein a nut is fixed on the sliding block; a screw rod is fixed on an output shaft of the piston driving device; the nut is installed on the screw rod.

* * * * *